(12) United States Patent
Da Silva et al.

(10) Patent No.: US 7,013,173 B2
(45) Date of Patent: Mar. 14, 2006

(54) OPTICAL PROBE WITH REFERENCE FIBER

(75) Inventors: Luiz B. Da Silva, Danville, CA (US); Charles L. Chase, Dublin, CA (US)

(73) Assignee: The Regents of the University of California, Oakland, CA (US)

( * ) Notice: Subject to any disclaimer, the term of this patent is extended or adjusted under 35 U.S.C. 154(b) by 198 days.

(21) Appl. No.: 09/997,872

(22) Filed: Nov. 29, 2001

(65) Prior Publication Data

US 2003/0100836 A1    May 29, 2003

(51) Int. Cl.
*A61B 5/00* (2006.01)
(52) U.S. Cl. ............... 600/477; 356/450; 356/451
(58) Field of Classification Search ........ 600/473–478, 600/407, 160; 356/450, 451
See application file for complete search history.

(56) References Cited

U.S. PATENT DOCUMENTS

| 5,303,026 | A |   | 4/1994  | Strobl et al. ............. 356/318 |
| 5,348,019 | A | * | 9/1994  | Sluss et al. .............. 600/480 |
| 5,349,954 | A |   | 9/1994  | Tiemann et al. .......... 128/634 |
| 5,708,273 | A | * | 1/1998  | VonBargen ............. 250/341.2 |
| 5,792,053 | A |   | 8/1998  | Skladnev et al. ........... 600/407 |
| 5,800,350 | A |   | 9/1998  | Coppleson et al. ......... 600/372 |
| 5,941,834 | A |   | 8/1999  | Skladnev et al. ........... 600/587 |
| 6,026,323 | A |   | 2/2000  | Skladnev et al. ........... 600/547 |
| 6,109,270 | A |   | 8/2000  | Mah et al. ................ 128/920 |
| 6,137,108 | A | * | 10/2000 | DeThomas et al. ..... 250/339.07 |
| 6,377,840 | B1| * | 4/2002  | Gritsenko et al. .......... 600/476 |
| 6,485,413 | B1| * | 11/2002 | Boppart et al. ............ 600/160 |
| 6,564,087 | B1| * | 5/2003  | Pitris et al. ................ 600/478 |
| 6,594,518 | B1| * | 7/2003  | Benaron et al. ............ 600/477 |

FOREIGN PATENT DOCUMENTS

| EP | 0 582 686 B1 | 8/1998 |
| EP | 0 872 211 B1 | 7/2000 |
| EP | 1 092 385 A2 | 4/2001 |

\* cited by examiner

*Primary Examiner*—Eleni Mantis Mercader
(74) *Attorney, Agent, or Firm*—Eddie E. Scott; Alan H. Thompson

(57) ABSTRACT

A system for characterizing tissue includes the steps of generating an emission signal, generating a reference signal, directing the emission signal to and from the tissue, directing the reference signal in a predetermined manner relative to the emission signal, and using the reference signal to compensate the emission signal. In one embodiment compensation is provided for fluctuations in light delivery to the tip of the probe due to cable motion.

2 Claims, 3 Drawing Sheets

OPTICAL PROBE WITH REFERENCE FIBER

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of Endeavor

The present invention relates to tissue recognition and more particularly to a probe system for tissue recognition.

2. State of Technology

A New Release dated Jan. 10, 2001 by the Lawrence Livermore National Laboratory operated by the University of California provides the following information, "The pain and anxiety women experience undergoing breast cancer tests and awaiting the results may soon be lessened thanks to a new, minimally invasive diagnostic tool that can instantly detect cancerous tissue. Lawrence Livermore National Laboratory has partnered with San Jose-based BioLuminate, Inc. to develop "Smart Probe," a tool for earlier, more accurate breast cancer detection that removes no tissue and is expected to achieve accuracy levels comparable to surgical biopsies in detecting cancerous cells.

The BioLuminate "Smart Probe," smaller than the needle used in routine blood tests, is inserted into breast tissue after an initial screening indicates an area of concern. The probe looks for multiple known indicators of breast cancer, instantaneously providing physicians with information they can use to determine whether more invasive and costly tests are necessary. The results of the "Smart Probe" procedure are immediately available to patients, helping relieve anxiety. First human studies using the device are expected to begin this spring at sites to be selected in Northern California. "Physicians have been seeking a way to acquire more specific information about a suspected cancer site before performing a biopsy or surgery," said Neil Gorrin, MD, Assistant Chief of Surgery at Kaiser Permanente Medical Center in South San Francisco. "The "Smart Probe" not only is less invasive, but it provides several specific measurements of known cancer indicators in real time, which will improve our chances of making the right diagnosis and treatment plan for the patient."

Fewer Unnecessary Biopsies—Breast cancer is the second leading cause of death among women in the United States. Last year in the U.S., 182,800 women were diagnosed with breast cancer and more than 40,800 died of the disease. In the U.S. each week, approximately 16,000 women undergo unnecessary, surgical breast biopsies on suspicious tissue that turns out benign. In addition, physicians miss about 4,600 cases of breast cancer each week during physical examinations and mammogram reviews. "By using the BioLuminate 'Smart Probe' before biopsies are performed on suspicious lesions, many unnecessary surgeries can be eliminated," said Richard Hular, President and CEO of BioLuminate. "Not only is this a great benefit for the patient, it also has the potential to save the U.S. healthcare system over $2 billion annually."

Cancer Indicators Measured in Real Time—Once a mammogram or physical exam has detected a possible malignant lump, "Smart Probe" is inserted into the tissue and guided to the suspicious region. Sensors on the tip of the probe measure optical, electrical and chemical properties that are known to differ between healthy and cancerous tissues. The "Smart Probe" can detect multiple (5 to 7) known indicators of breast cancer. Tissue measurements are made in real time in both normal and suspect tissue. "Smart Probe's" sensors begin gathering information the moment the probe is inserted into tissue. Computer software compares the real-time measurements to a set of known, archived parameters that indicate the presence or absence of cancer. The results are displayed instantly on a computer screen. "The key technology and experience that Lawrence Livermore Lab has to offer will allow the 'Smart Probe' to be much smaller than first conceived, and acquire data more accurately," said Luiz Da Silva, Ph.D, Livermore's Associate Medical Technology Program Leader and primary investigator for the "Smart Probe." "In addition, we will have the capacity to add additional measurements if necessary."

U.S. Pat. No. 5,303,026 for apparatus and method for spectroscopic analysis of scattering media by Karlheinz Strobl, Irving J. Bigio, and Thomas R. Loree, patented Apr. 12, 1994 provides the following background information, "Attempts at in situ real-time diagnostics for complex biological media, have been only marginally successful because of limitations in the spectroscopic techniques that are applicable. Conventional fluorescence spectroscopy is generally unable to resolve differences among similar biological tissue samples (or subtle differences in a given tissue sample) and has generally not proven reliable in detecting malignancy except with the aid of drugs such as hematoporphyrin derivatives which are used as targeting fluorescers."

U.S. Pat. No. 5,349,954 for a tumor tissue characterization apparatus and method by Jerome J. Tiemann and Fay A. Marks, patented Sep. 27, 1994 provides the following background information, "In a conventional procedure, a radiologist performs x-ray mammography. If an abnormal breast process recorded on the resulting mammograms is considered suspicious, a surgical biopsy can be ordered. Immediately prior to the biopsy, the radiologist takes several more views or projections of the breast during preoperative localization of the abnormality and marks the location of the suspicious abnormality by impaling the region with a thin, hooked guide wire. The patient is then taken to an operating room and a surgeon performing the biopsy follows the hooked wire guide to the precise location of the suspected abnormality. The most common form of biopsy involves surgically removing the suspected region. One of the less invasive forms of biopsy, stereotactic fine needle aspiration biopsy, aspirates a small amount of cells for cytologic analysis. The advantages of this technique are that it is minimally invasive, is accurate to less than 2 mm in lesion localization, has a sensitivity greater than 90%, and is less expensive than surgical biopsies. But since small (22 gauge) needles are used, cytology on the small amount of material removed is not easy. Far more accurate is large-core needle biopsy (using stereotactic positioning or ultrasound guidance), another alternative to surgical biopsy. Core biopsies remove a 1 mm.times.17 mm core of tissue (if a 14 gauge needle is used) for standard histological examination. However, benign histological diagnoses are difficult to make. In fact, for both fine needle aspiration biopsy and core biopsy, the techniques are only useful when they return a positive result for malignancy. In all other cases, the suspicious lesion must undergo incisional or excisional surgical biopsy. False negatives in analyzing an x-ray mammogram occur when benign tumors or "normal" breast tissue with radiological densities similar to cancer completely or partially mask a malignant tumor which does not exhibit primary or secondary mammographic signs of carcinema. False positives are also problematic because they reduce the acceptability of mammography by the general public and lead to unnecessary biopsies."

U.S. Pat. No. 5,800,350 for an apparatus for tissue type recognition by Coppleson et al, patented Sep. 1, 1998, provides the following background information, "The early detection of tissues displaying pre-cancer or cancer modifications is important for successful medical treatment. Presently-used detection techniques suffer from inaccuracy and are subject to operator error as well as being time-consuming. A good example of this is the Pap smear for cervical cancer. X-ray diagnosis, which can also be used for detecting advanced cancer modifications, can lead to detrimental exposure to radiation. A positive result produced by a Pap smear test is generally followed by a visual examination using a colposcope which provides a magnified view of the cervix. Suspect regions of the cervix are evaluated by a skilled practitioner who then makes a subjective judgement of the tissue observed. There are many tissue types in the cervix, some of which display analogous appearances, including visual and textural characteristics, that make clinical diagnosis very difficult and subject to error. Similar subjective assessments play a major role in the detection and treatment of other locations of neoplastic pre-activity and activity, for example skin melanoma. Methods and devices have been developed in an attempt to use measurements of physical characteristics of the tissue for distinguishing cancerous tissue from non-cancerous tissue. Electrical measurements of the skin or tissue have been used. Such electrical measurements on their own do not provide the information needed for an effective diagnosis."

U.S. Pat. No. 6,026,323 for a tissue diagnostic system by Skladnev et al, patented Feb. 15, 2000, provides the following background information, "The identification of tissue type based upon responses to incident light and/or electrical stimulation is well known. This has led to diagnostic techniques and apparatus for identifying tissue types such as cancerous or pre-cancerous. Existing techniques for identifying cancers run the gamut from microscopic examination of tissue smears by trained cell pathologists, to the study of the fluorescence, electrical and other physical properties of tissues. Much research has been devoted to the identification and comparison of optical and electrical characteristics of healthy and damaged tissue in the hope that it could lead to new diagnostic techniques."

U.S. Pat. No. 6,109,270 for a multimodality instrument for tissue characterization by Robert W. Mah and Russell J. Andrews, patented Aug. 29, 2000 provides the following background information, "Existing medical instruments provide general diagnoses for the detection of tissue interface such as normal tissue, cancer tumor, etc. However, such detection has been limited clinically to tactile feedback, temperature monitoring, and the use of a miniature ultrasound probe for tissue differentiation during surgical operations. Stereotactic computed tomography (CT) scanners, magnetic resonance imaging (MRI) devices, and similar other instruments provide guided brain biopsy and preoperative scans for use in neurosurgical surgeries. These scans allow samples of brain tissue to be obtained with some degree of accuracy. However, existing devices provide diagnostic data of limited use, particularly in neurosurgery, where the needle used in the standard stereotactic CT or MRI guided brain biopsy provides no information about the tissue being sampled. The tissue sampled depends entirely upon the accuracy with which the localization provided by the preoperative CT or MRI scan is translated to the intracranial biopsy site. Any movement of the brain or the localization device (e.g., either a frame placed on the patient's head, or fiducials/anatomical landmarks which are in turn related to the preoperative scan) results in an error in biopsy localization. Also, no information about the tissue being traversed by the needle (e.g., a blood vessel) is provided. Hemorrhage due to the biopsy needle severing a blood vessel within the brain is the most devastating complication of stereotactic CT or MRI guided brain biopsy."

SUMMARY OF THE INVENTION

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for characterizing tissue. A generation system generates an emission signal and a reference signal. A probe directs the emission signal to the tissue. A transmission system transmits the emission signal to and from the probe and transmits the reference signal in a predetermined manner relative to the emission signal. A compensation system utilizes the reference signal to correct the emission signal. In one embodiment the system includes the steps of generating an emission signal, generating a reference signal, directing the emission signal to and from the tissue, directing the reference signal in a predetermined manner relative to the emission signal, and using the reference signal to compensate the emission signal. In one embodiment the reference signal provides compensation for fluctuations in light delivery to the tip of the probe due to cable motion.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
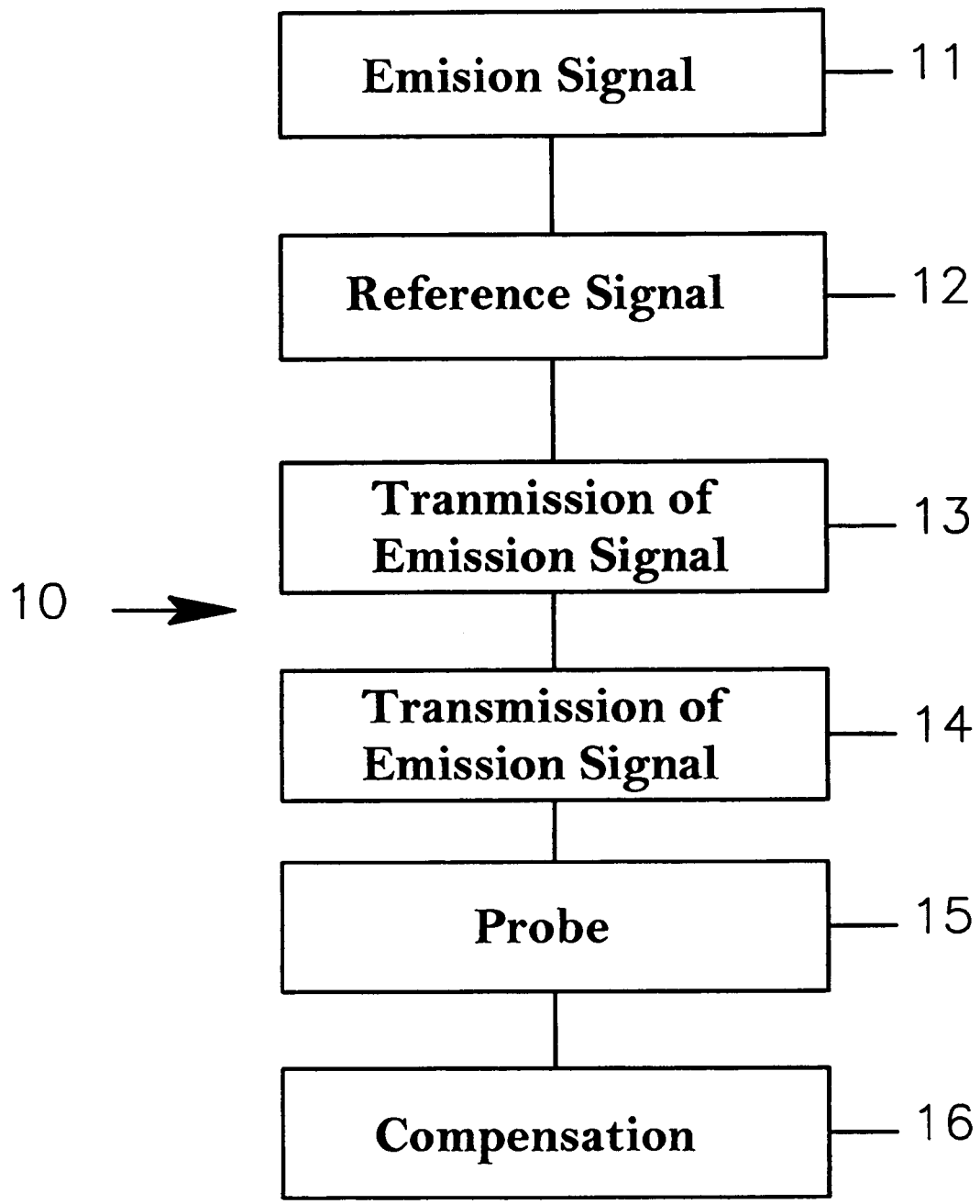
FIG. 1 illustrates an embodiment of a system constructed in accordance with the present invention.

Referring now to the drawings, to the following detailed information, and to incorporated materials; a detailed description of the invention, including specific embodiments, is presented. The detailed description serves to explain the principles of the invention. The invention is susceptible modifications and alternative forms. The invention is not limited to the particular forms disclosed. The invention covers all modifications, equivalents, and alternatives falling within the spirit and scope of the invention as defined by the claims.

The present invention provides a system for characterizing tissue. The present invention includes a method incorporating the steps of generating an emission signal, generating a reference signal, directing the emission signal to and from the tissue, directing the reference signal in a predetermined manner relative to the emission signal, and using the reference signal to compensate the emission signal. In one embodiment, compensation is provided for fluctuations in light delivered to the tip of the probe caused by cable motion. An emission signal and a reference signal are generated. The emission signal is directed to a probe. The probe directs the emission signal to the tissue. The reference signal is directed in a manner relative to the emission signal. A compensation system utilizes the reference signal to correct the emission signal.

Embodiments of the present invention are supplemented by technical details of known probe systems. Some of the probe systems are described in publications. An apparatus and method for spectroscopic analysis of scattering media is described in U.S. Pat. No. 5,303,026 by Karlheinz Strobl, Irving J. Bigio, and Thomas R. Loree, patented Apr. 12, 1994. The disclosure of this patent is incorporated herein in its entirety by reference. A tumor tissue characterization apparatus and method is described in U.S. Pat. No. 5,349,954 by Jerome J. Tiemann and Fay A. Marks, patented Sep. 27, 1994. The disclosure of this patent is incorporated herein in its entirety by reference. An apparatus for tissue type recognition is described in U.S. Pat. No. 5,800,350 by Coppleson et al, patented Sep. 1, 1998. The disclosure of this patent is incorporated herein in its entirety by reference. A tissue diagnostic system is described in U.S. Pat. No. 6,026,323 by Skladnev et al, patented Feb. 15, 2000. The disclosure of this patent is incorporated herein in its entirety by reference. A multimodality instrument for tissue characterization is described in U.S. Pat. No. 6,109,270. The disclosure of this patent is incorporated herein in its entirety by reference. A multisensor probe for identifying cancerous tissue in vivo is described in U.S. Patent Application No. 2003/0045798 by Richard Hular et al, published Mar. 6, 2003. The disclosure of this patent application is incorporated herein in its entirety by reference.

Referring now to FIG. 1, a system constructed in accordance with the present invention is illustrated. The system is generally designated by the reference numeral 10. The system 10 generates an emission signal 11 and a reference signal 12. The emission signal 11 is directed to a probe 15 as illustrated by transmission of emission signal 13. The reference signal is directed toward the probe 15 in a manner that is relative to the emission signal as illustrated by transmission of reference signal 14. The probe is inserted into the tissue. The probe measures tissue properties and the information is returned as illustrated by transmission of emission signal 13. The reference signal is returned as illustrated by transmission of reference signal 14. As illustrated in FIG. 1, compensation 16 is provided by using the reference signal to compensate the emission signal.

In one embodiment the emission signal transmission system includes an optical illumination fiber and an optical collection fiber. In one embodiment the reference signal transmission system includes an optical splitter. One embodiment of the present invention includes a probe with a needle, a cable that connects the probe to a control module, optical sources such as a laser, multiple lasers, or white light sources, and a fiber optic splitter that splits light from the sources into an emission fiber and a reference fiber. In this embodiment, the reference fiber goes to the probe and returns to a detector. The reference fiber preferably extends into the handle of the probe and not into the needle.

The present invention includes a method incorporating the steps of generating an emission signal, generating a reference signal, directing the emission signal to and from the tissue, directing the reference signal in a predetermined manner relative to the emission signal, and using the reference signal to compensate the emission signal. For example, compensation may be provided for fluctuations in light delivery to the tip of the probe due to cable motion by measuring signals of the reference fiber. Fluctuations may occur for a variety of reasons including losses through the fiber due to bends in the fiber. Each of the optical fibers in the probe likely experience similar losses as the reference fiber. Accuracy is increased in an embodiment wherein the fibers have a similar numerical aperture, material properties and are tightly packed. The fibers can also be bonded within the cable. The fibers can be bonded using a soft polymer compound or silicone. The reference fiber that is integrated into the probe cable improves the device accuracy by reducing the effects of optical source fluctuations and changes in the fiber optic efficiency.

The present invention includes a reference fiber that accounts for changes in the efficiency of the probe fiber optics. Fiber optic losses can change as the fiber optic is bent. Most optical probes rely on long fiber optic cables that connect to hard metal probes that don't bend. However, cable movement can produce a time dependent change in the cable transmission efficiency. In one embodiment a fiber optic splitter directs a fraction of the total light into a reference fiber that is built into the cable of the probe. The reference fiber goes to the end of the cable and returns to the control box where the light is measured using an optical detector.

An embodiment of the optical probe with a reference fiber of the present invention can be used to determine human tissue type and/or state. Another embodiment of the probe can be used to determine whether tissue is malignant or benign. Another embodiment of the probe can be used to perform tissue biopsies without removing tissue.

Figure 2:
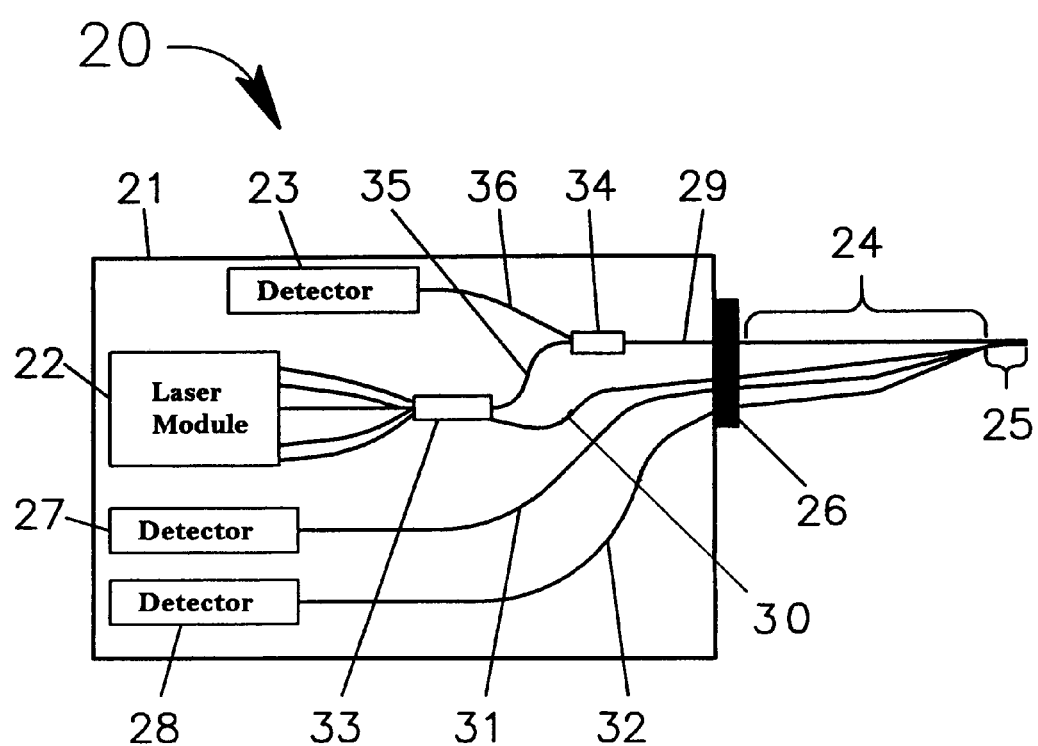
FIG. 2 illustrates another embodiment of a system constructed in accordance with the present invention.

Referring now to FIG. 2 an optical probe system, generally designated by the reference numeral 20, is illustrated. A laser module 22 contains multiple laser sources that are each coupled to a fiber optic. The lasers are combined through a splitter 33 and then split into two outputs 30 and 35. A reference fiber 30 that takes a small fraction (e.g 5–10%) and then goes into the handle of the probe 25. The other output 35 from the splitter (~90%) goes to another fiber 29 which couples to a third fiber optic splitter 34. The third fiber optic splitter 34 transmits light into the emission fiber 29 that goes into the optical probe 25. The light collected by the emission fiber 29 returns through the splitter 34 and 90% goes into a fiber 36 that is used to measure the backscatter or fluorescence.

The optical collection fiber 32 within the probe 25 delivers light to the optical detector 28. The other end of the reference fiber 31 is coupled to another detector 27. The reference fiber forms a loop (see 30 and 31) that goes from the control unit 21 through the smart probe cable 24, to the smart probe handle and then returns. The reference fiber does not enter the needle section of the smart probe. This technique will allow fluctuations in light delivery to the tip of the device due to cable motion to be partly accounted for. These fluctuations occur because losses through the fiber are affected by any changes in the bends in the fiber. This assumes that all the fibers experience similar changes. To increase the probability of this the fibers should have a similar numerical aperture and material properties and be tightly packed and bonded within the cable. The fibers can be bonded using a soft polymer compound or silicone.

The intensity at the end of the collection fiber, $I_C$, is related to the laser intensity, $I_0$, the loss through a single pass of the fiber, L, and the effective coupling efficiency between emission and collection fiber, X, through the following expression.

$$I_C \propto I_0 L^2 X;$$

The coupling efficiency, X, includes the geometrical coupling efficiency between the fibers and the tissue absorption and scattering properties. Note that both L and X are wavelength dependent.

The intensity at the end of the reference fiber, $I_R$, is related to the laser intensity, $I_0$, the loss through a single pass of the fiber, L, and the coupling fraction between emission fiber and the reference fiber, A, through the following expression.

$$I_R \propto A I_0 L^2;$$

If we take the ratio of the two intensities we have $$\frac{I_D}{I_R} \propto \frac{X}{A}$$

Using a calibrated laboratory system where we accurately know A, we can determine X in the calibration medium for each probe. This information can be encoded into the device (bar code, etc.) and used by the analysis software to determine A for each probe and system when the probe calibration step is performed by the clinical unit. After this step the device can be used to accurately measure, X, which is related to the tissue properties.

Figure 3:
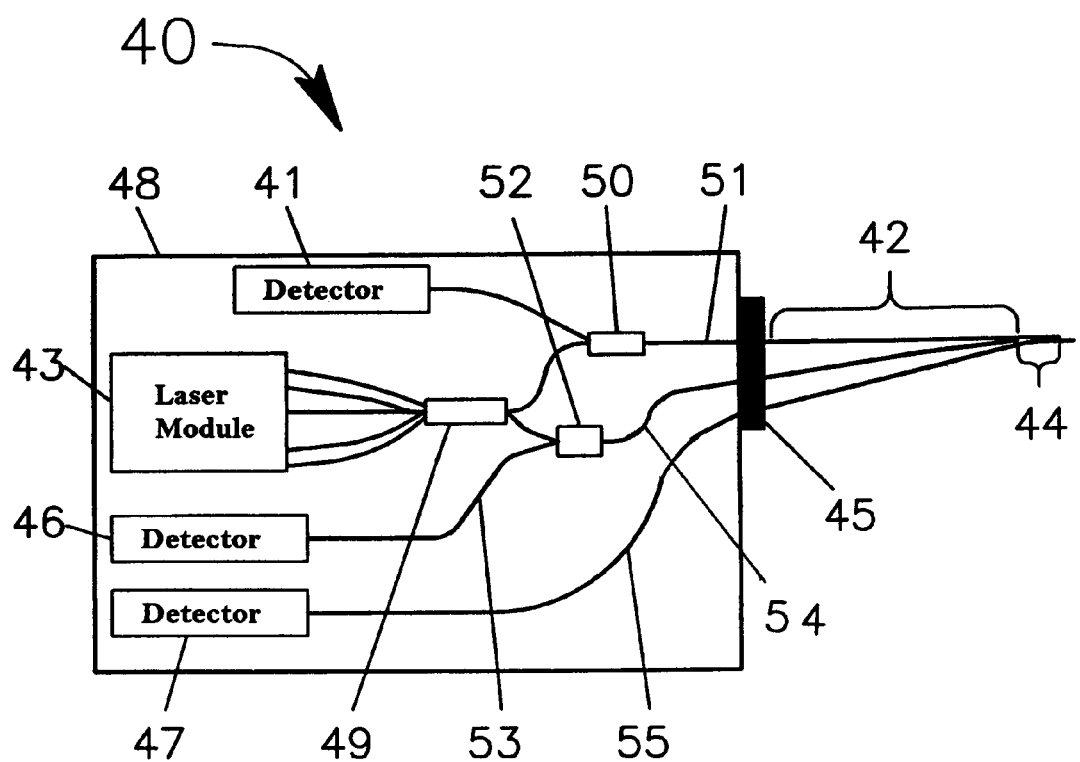
FIG. 3 illustrates yet another embodiment of a system constructed in accordance with the present invention.

Referring now to FIG. 3 another embodiment of the present invention is shown. This embodiment is generally designated by the reference numeral 40. It reduces the number of fiber optics at the connector to the system by incorporating an additional splitter 52 within the system.

In this embodiment the reference fiber 54 terminates in the handle of the probe 44 and the end is coated with a reflective layer (e.g. aluminum, chromium, silver). The reflected light returns through the reference fiber 54 and at the fiber optic splitter 52 a fraction is directed to the detector 46. As in FIG. 2, light is transmitted through the probe 44 and onto the tissue by the emission fiber 51. A collection fiber 55 collects the scattered light and delivers it to detector 47.

The reference fiber 55 does not enter the probe. This minimizes the diameter of the probe 44. However, if probe size is not a concern then the reference fiber can continue into the probe.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system for producing a signal adapted to characterize tissue and to correct for optical fluctuations, consisting of:
   a laser module for generating an emission signal and a reference signal,
   a splitter connected to said laser module for splitting said emission signal and said reference signal,
   a probe with a needle that is adapted to be inserted into the tissue and that directs said emission signal to the probe and through the needle to the tissue for characterizing the tissue,
   an emission optical detector,
   a reference optical detector,
   a transmission system including
   an emission optical fiber connected to said said splitter, to said probe, to said needle, and to said emission optical detector that transmits said emission signal to said probe, to said needle, and from said probe to the tissue for characterizing the tissue, and from the tissue to said needle, to said probe and to said emission optical detector, and
   a reference optical fiber connected to said said splitter, to said probe, and to said reference optical detector that transmits said reference signal to said probe and from said probe to said reference optical detector, and
   a compensation system that utilizes said reference signal to correct said emission signal and producing a signal for characterizing the tissue for the optical fluctuations.

2. The system for producing a signal adapted to characterize tissue of claim 1, wherein said laser module comprises multiple lasers that generate said optical emission signal and said optical reference signal.

* * * * *